United States Patent
Torashima et al.

(10) Patent No.: US 8,767,278 B2
(45) Date of Patent: Jul. 1, 2014

(54) ELECTROMECHANICAL TRANSDUCER AND PHOTOACOUSTIC APPARATUS

(75) Inventors: Kazutoshi Torashima, Yokohama (JP); Yuji Kasanuki, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 76 days.

(21) Appl. No.: 13/421,791

(22) Filed: Mar. 15, 2012

(65) Prior Publication Data
US 2012/0262770 A1    Oct. 18, 2012

(30) Foreign Application Priority Data

Apr. 14, 2011   (JP) ................................ 2011-090123

(51) Int. Cl.
*G02B 26/08*   (2006.01)
(52) U.S. Cl.
USPC ....................................................... 359/199.2
(58) Field of Classification Search
CPC ............... G02B 26/08; G02B 26/0916; G02B 26/0825; G02B 26/0833; G02B 26/0841; G02B 26/085; G02B 26/10
USPC .............. 310/313 B; 359/199.2, 198.1–226.1
See application file for complete search history.

(56) References Cited

U.S. PATENT DOCUMENTS

| | | | |
|---|---|---|---|
| 5,317,152 A | 5/1994 | Takamatsu et al. | |
| 5,357,108 A | 10/1994 | Suzuki et al. | |
| 5,390,161 A | 2/1995 | Kurihara et al. | |
| 5,481,527 A | 1/1996 | Kasanuki et al. | |
| 5,838,097 A | 11/1998 | Kasanuki et al. | |
| 8,144,327 B2 | 3/2012 | Nakajima et al. | 356/432 |
| 8,540,640 B2 | 9/2013 | Sano et al. | |
| 2010/0038993 A1* | 2/2010 | Umeda et al. | 310/313 B |
| 2010/0319453 A1 | 12/2010 | Ichihara et al. | 73/596 |

FOREIGN PATENT DOCUMENTS

| | | |
|---|---|---|
| JP | 2010-75681 | 4/2010 |
| JP | 2011-4790 | 1/2011 |
| JP | 2011-97991 | 5/2011 |

OTHER PUBLICATIONS

U.S. Appl. No. 13/425,346, filed Mar. 20, 2012, by Kazutoshi Torashima et al.

* cited by examiner

*Primary Examiner* — Euncha Cherry
(74) *Attorney, Agent, or Firm* — Fitzpatrick, Cella, Harper & Scinto

(57) ABSTRACT

The present invention provides an electromechanical transducer which can prevent light from being incident on a receiving face, without deteriorating mechanical characteristics of a vibration film. The electromechanical transducer has at least one cell 2 in which the vibration film 7 containing one electrode 8 out of two electrodes 3 and 8 that are provided so as to interpose a space 5 therebetween is vibratably supported. The electromechanical transducer has a stress relaxation layer 9 formed on the vibration film 7, which has an acoustic impedance matching that of the vibration film 7, and has a light reflection layer 6 formed on the stress relaxation layer 9.

22 Claims, 2 Drawing Sheets

ELECTROMECHANICAL TRANSDUCER AND PHOTOACOUSTIC APPARATUS

BACKGROUND OF THE INVENTION

1. Field of the Invention

The present invention relates to an electromechanical transducer such as a capacitance type electromechanical transducer which is used as an ultrasonic transducer or the like, and to a photoacoustic apparatus.

2. Description of the Related Art

Conventionally, a micro-mechanical member to be manufactured with a micro-machining technology can be processed in a micro-metric order, and various micro-functional elements are realized by using these members. A capacitance type electromechanical transducer such as CMUT (Capacitive Micromachined Ultrasonic Transducer) using such a technology has been studied as an alternative of a piezoelectric element. Such a capacitance type electromechanical transducer can transmit and receive an acoustic wave such as an ultrasonic wave by using the vibration of a vibration film, and it can easily obtain superior broad band characteristics particularly in a liquid. On the other hand, an ultrasonic transducer has been proposed, which illuminates an object to be measured with an illumination light (near-infrared rays or the like) and receives a photoacoustic wave thereby emitted from an inside of a subject (see Japanese Patent Application Laid-Open No. 2010-075681). The mentioned transducer is provided with a light reflection member for reflecting a light, and this light reflection member is structured so as to be larger than receiving faces of the ultrasonic transducer which receive the photoacoustic wave.

SUMMARY OF THE INVENTION

In a case a capacitance type electromechanical transducer is used as a sensor for receiving a photoacoustic wave, when a light for generating the photoacoustic wave is incident on the transducer, a photoacoustic wave is generated in the receiving face of the transducer to cause a noise. In Japanese Patent Application Laid-Open No. 2010-075681, in order to prevent such a situation, the reflection member is arranged just before the receiving face of the capacitance type electromechanical transducer so that the light is not incident on the transducer. As an improvement of the prior art, there is a need to reduce a change of the spring constant of the vibration film constituting the transducer and dispersion of the deformation amounts of the vibration film, to thereby efficiently prevent the degradation and dispersion of sensitivity and the reduction of band width.

An electromechanical transducer according to the present invention is designed with respect to the above described problems, and has at least one cell in which a vibration film containing one electrode out of two electrodes that are provided so as to interpose a space therebetween is vibratably supported. The electromechanical transducer includes a stress relaxation layer provided on the vibration film, and a light reflection layer provided on the stress relaxation layer.

The electromechanical transducer according to the present invention has the stress relaxation layer provided on the vibration film which is a receiving face of the transducer, and has the light reflection layer provided thereon. Accordingly, the receiving face is not affected so much by a stress of the light reflection layer, and accordingly the vibration film resists causing deformation and the like therein. Thereby, the electromechanical transducer having the light reflection layer formed therein can lower the dispersion of its performance, and can receive an elastic wave such as a photoacoustic wave.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

The electromechanical transducer according to the present invention has a feature of providing a stress relaxation layer on a vibration film of a cell, and providing a light reflection layer on the stress relaxation layer. The cell is formed of, for instance, a substrate, a first electrode in one surface side of the substrate, the vibration film having a second electrode, and a vibration film supporting portion which supports the vibration film so as to form a space between the first electrode and the vibration film. The cell can be produced with a so-called sacrificial type method, a bonded type method and the like. The examples of FIG. 1A and FIG. 1B have a structure which can be produced with the bonded type method, and the example of FIG. 2 has a structure which can be produced with the sacrificial type method.

Figure 1A:
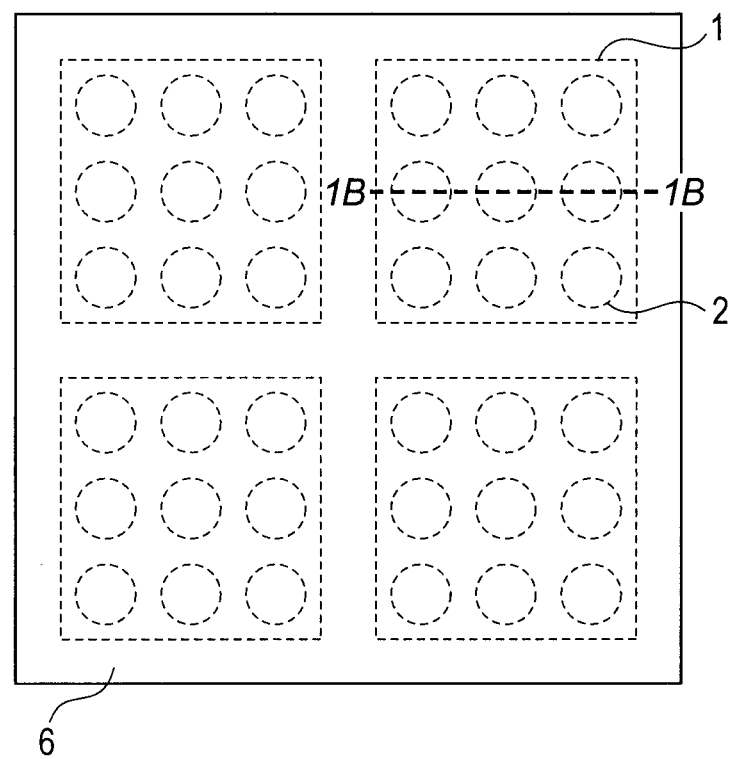
FIG. 1A is a view illustrating an electromechanical transducer in an embodiment and Exemplary Embodiment 1 of the present invention.
Figure 1B:
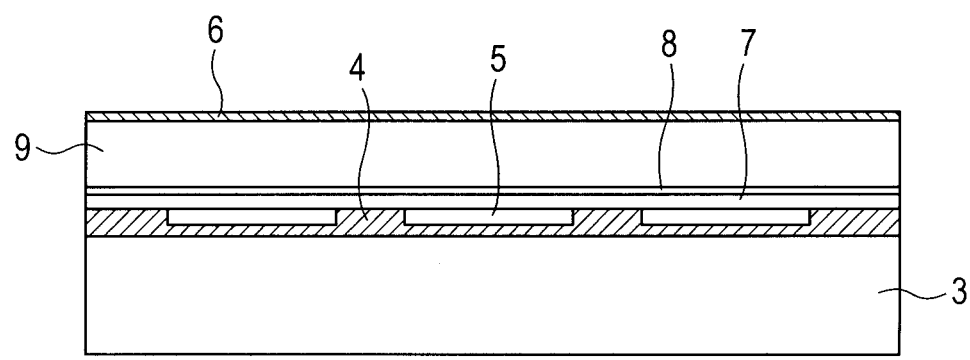
FIG. 1B is a sectional view taken along 1B-1B of FIG. 1A.

One embodiment of the present invention will be described below with reference to FIG. 1A and FIG. 1B. FIG. 1A is a top plan view of a capacitance type electromechanical transducer of the present embodiment; and FIG. 1B is a sectional view taken along line 1B-1B of FIG. 1A. The present electromechanical transducer has a plurality of elements 1 having a cell 2 therein. In FIG. 1A and FIG. 1B, although only four elements 1 are provided, the number of the elements may be any number. In addition, although each element 1 includes nine cells 2, the number of the cells 2 may be any number.

The cell 2 of the present embodiment includes a vibration film 7, a space 5 such as a void, a vibration film supporting portion 4 which vibratably supports the vibration film 7, and a silicon substrate 3. The vibration film 7 is exemplified as a single-crystal silicon, or it may also be a film-formed vibration film (for instance, silicon nitride film) formed with a stacking technique. The vibration film 7 has a metal (aluminum thin-film 8 or the like) which becomes a second electrode provided in the vibration film or on the outer face of the vibration film. In the present invention, the assembly of a membrane portion formed of the silicon nitride film or a single-crystal silicon film and the second electrode portion is referred to as the vibration film. However, when the vibration film 7 is single-crystal silicon with low resistance, the single-crystal silicon can be used as the second electrode, and consequently the metal which becomes the second electrode may not be arranged. The silicon substrate 3 has low resistance, and it can be used as the first electrode. When the silicon substrate is not used as the first electrode, a metal can be formed on the substrate as the first electrode. Also in the case where an insulating substrate such as a glass substrate is used as the substrate, the first electrode is formed on the substrate. The first and second electrodes are provided so as to interpose the space 5 therebetween.

The electromechanical transducer of the present embodiment has a stress relaxation layer 9 on a receiving face for an acoustic wave. The stress relaxation layer 9 is formed directly on the vibration film when the first electrode is formed in the vibration film, or it is formed on the first electrode when the first electrode is formed on the vibration film. It is desirable to arrange the stress relaxation layer 9 so as to be larger than the total surface of the receiving faces including all the cells. The stress relaxation layer is a layer which does not increase the deformation amount of the vibration film 7 and which does not change mechanical characteristics such as a spring constant of the vibration film 7. In addition, the stress relaxation layer can have an approximately same level of acoustic impedance as that of the receiving face having the vibration film 7. Specifically, the Young's modulus can be 0 MPa or more and 100 MPa or less, and the acoustic impedance can be 1 MRayls or more and 2 MRayls or less. If the stress relaxation layer has the Young's modulus of 100 MPa or less, the stress relaxation layer relaxes the influence of the stress of the light reflection layer 6 (which will be described later) on the vibration film, and it does not almost change the mechanical characteristics of the vibration film 7 because of having sufficiently low stiffness (Young's modulus). In addition, when the stress relaxation layer has the acoustic impedance of 1 MRayls or more and 2 MRayls or less, the stress relaxation layer has an approximately same level of the acoustic impedance as that of the receiving face for the acoustic wave, and hence it can reduce the reflection of the acoustic wave at an interface between the vibration film 7 and the stress relaxation layer 9. The acoustic impedance of the receiving face can be converted from the spring constant and mass of the vibration film, the capacitance of an element and the like, and it is 0.01 to 5 MRayls in the case, for instance, of CMUT having a central frequency of 1 to 10 MHz. However, the acoustic impedance of the receiving face varies depending on the shape of the cell and the like. When the electromechanical transducer of the present embodiment is used in a medium such as water having a low acoustic impedance (where the acoustic impedance of water is approximately 1.5 MRayls), if the acoustic impedance of the stress relaxation layer is 1 MRayls or more and 2 MRayls or less, the electromechanical transducer can reduce the reflection at the interface between the stress relaxation layer and the medium.

The electromechanical transducer of the present embodiment has a light reflection layer 6 provided on the stress relaxation layer 9. The light reflection layer 6 is a layer mainly for reflecting the light with a wavelength which is emitted from a light source to be used for irradiating a subject to generate a photoacoustic wave, and it may be a membrane that shows a high reflectance with respect to the wavelength which the light source has. As the light reflection layer 6, Al, Au, a dielectric multilayer and the like are used. It is desirable to arrange the light reflection layer 6 on the whole face of the stress relaxation layer 9. It is more desirable to arrange the light reflection layer 6 on all members which are positioned closer to the subject side than the receiving face, in the electromechanical transducer. With the present structure a noise which is generated in the electromechanical transducer by irradiation with a laser beam can be prevented. The reflectance of the light reflection layer 6 with respect to the light to be used for the electromechanical transducer can be 80% or more, and can further be 90% or more. In addition, the light reflection layer 6 can desirably be thin, because the light reflection layer 6 is arranged on the receiving face and accordingly it needs to propagate the acoustic wave through the light reflection layer 6 without almost attenuating the acoustic wave. The light reflection layer can have a thickness specifically of 10 μm or less.

The drive principle of the electromechanical transducer of the present embodiment is as follows. An element 1 is formed on a silicon substrate 3 which is used as a first electrode, and a vibration film 7 is used as a second electrode. With the element 1, an electric signal can be drawn from the first electrode or the second electrode by providing a not-shown drawing wire on the substrate, or in the substrate that is a through-hole substrate. When receiving an acoustic wave, a direct-current voltage is applied to the first electrode or the second electrode beforehand with a not-shown voltage application unit. When the electromechanical transducer receives the acoustic wave, the vibration film 7 is deformed, and consequently a distance of a space 5 between the vibration film 7 containing the second electrode and the substrate 3 which is the first electrode changes. Thereby, the capacitance changes. An electric current passes in a not-shown drawing wire due to the change of the capacitance. The electromechanical transducer can receive the acoustic wave by converting this electric current into voltage with a not-shown current/voltage conversion element. The electromechanical transducer also can vibrate the vibration film 7 of a single-crystal silicon with an electrostatic force, by applying a direct-current voltage and an alternating-current voltage to the silicon substrate 3 which is the first electrode, or to the vibration film 7 which is the second electrode. Thereby, the electromechanical transducer can also transmit the acoustic wave.

The capacitance type electromechanical transducer of the present embodiment can be used for receiving a photoacoustic wave. The photoacoustic wave is an acoustic wave (typically, ultrasonic wave) which is generated from a subject having absorbed the light that has irradiated the subject with a short pulse laser. Accordingly, the not-shown subject needs to be irradiated with a light such as a laser. When a scattered light and the like emitted from the light source of this laser and the like are incident on the receiving face of the transducer, the vibration film 7 constituting the receiving face absorbs the scattered light and the like emitted from the light source to result in generating the acoustic wave in the receiving face, which may cause a noise. In order to prevent the noise, the light reflection layer is used, but in the case of the capacitance type electromechanical transducer having the light reflection layer directly provided on the receiving face, mechanical characteristics such as the deformation amount of the vibration film and the spring constant of the vibration film may change due to a stress or the like of the light reflection layer. Then, the sensitivity dispersion between each cell and between each element, and the band dispersion may occur. In contrast to this, the capacitance type electromechanical transducer of the present embodiment has the light reflection layer 6 provided on the stress relaxation layer 9. Since the stress relaxation layer 9 has a small Young's modulus, even when the stress relaxation layer is formed with a curing process, the stress relaxation layer can reduce the deformation of the vibration film and the change of the spring constant due to the stress or the like in the curing process. In addition, since the stress relaxation layer has a similar level of acoustic impedance to that of the receiving face, it can reduce the reflection of the acoustic wave which is received at an interface between the stress relaxation layer and the receiving face. Furthermore, since the capacitance type electromechanical transducer has the light reflection layer 6, a light is not incident on the receiving face. Consequently, when the transducer of the present embodiment is used as a sensor for receiving a photoacoustic wave, the noise can be reduced. In addition, since the light reflection layer 6 is arranged in the vicinity of the receiving face, the capacitance type electromechanical transducer can prevent the light such as the scattered light incident from various angles from being incident on the receiving face. In addition, since the light reflection layer 6 is integrated with the receiving face, the capacitance type electromechanical transducer which receives the photoacoustic wave can be down-sized, and it can be easily incorporated into another apparatus.

The capacitance type electromechanical transducer of the present embodiment can also have a supporting layer for a light reflection layer, which supports the light reflection layer, provided between the stress relaxation layer 9 and the light reflection layer 6 (see to Exemplary Embodiment 2 which will be described later). When the light reflection layer is film-formed directly on the stress relaxation layer, the light reflection layer is possibly warped or deformed due to the stress or the like of the light reflection layer, because the stress relaxation layer has a low Young's modulus. In addition, when the adhesiveness between the light reflection layer and the stress relaxation layer is low, the light reflection layer occasionally peels from the stress relaxation layer. In the present structure, the light reflection layer is formed on the supporting layer for the light reflection layer, which has stiffness higher than that of the stress relaxation layer, and accordingly the light reflection layer can be prevented from being warped or deformed, even when the supporting layer for the light reflection layer is bonded onto the stress relaxation layer. The Young's modulus of the supporting layer for the light reflection layer, which supports the light reflection layer 6, is desirably 100 MPa or more and 20 GPa or less. In addition, the light reflection layer is supported by the supporting layer for the light reflection layer, and the supporting layer for the light reflection layer and the stress relaxation layer can be bonded to each other with an adhesion method or an adhesive showing high adhesive strength. Accordingly, the structure with the use of the supporting layer for the light reflection layer can more surely prevent the light reflection layer from being warped or deformed and it can enhance the adhesive strength, compared to the case in which the light reflection layer is film-formed directly on the stress relaxation layer. The supporting layer for the light reflection layer, which supports the light reflection layer 6, may have an acoustic impedance of approximately 1 MRayls or more and 5 MRayls or less. It is possible to reduce the amount of the reflection of the acoustic wave at an interface between the supporting layer for the light reflection layer, which supports the light reflection layer 6, and the stress relaxation layer 9, by approaching the acoustic impedance of the supporting layer for the light reflection layer, which supports the light reflection layer 6, to that of the stress relaxation layer 9.

In the above described structure, the stress relaxation layer 9 is desirably made of polydimethylsiloxane (PDMS). The stress relaxation layer 9 may also be formed from: a material in which silica particles and the like are added into PDMS; fluorosilicone in which one part of hydrogens of the PDMS is substituted with fluorine; or a material in which the silica particles are added to the fluorosilicone. The acoustic impedance can be adjusted by the addition of the silica particles or the like. Since the PDMS has an acoustic impedance of approximately 1 MRayls to 2 MRayls, it can reduce the reflection of the acoustic wave at an interface between the stress relaxation layer and the receiving face. Furthermore, the PDMS has high compatibility with a living body. The supporting layer for the light reflection layer, which supports the light reflection layer 6, has desirably stiffness higher than that of the stress relaxation layer 9. When polydimethylsiloxane is used as the stress relaxation layer, such a supporting layer for a light reflection layer can be used as to be formed from a resin of, for instance, polymethylpentene, polycarbonate, acrylic, polyimide, polyethylene, polypropylene or the like. However, the materials for the supporting layer for the light reflection layer are not limited to these materials, as long as the supporting layer has the stiffness higher than that of the stress relaxation layer. Particularly, the acoustic impedance of trimethylpentene is approximately 1.8 MRayls, and the acoustic impedance of the polycarbonate is approximately 2.5 MRayls. The acoustic impedances are as low as 3 MRayls or less. Consequently, it is possible to reduce the amount of the reflection of the acoustic wave at the interface between the supporting layer for the light reflection layer, which supports the light reflection layer 6, and the stress relaxation layer 9. Furthermore, when the electromechanical transducer of the present embodiment is used in a medium having a low acoustic impedance, there is a small difference of the acoustic impedance between the supporting layer for the light reflection layer, which supports the light reflection layer 6, and the medium, and consequently the amount of the reflection of the acoustic wave at the interface therebetween can be reduced. Furthermore, the polycarbonate can decrease the surface roughness, consequently it can decrease also the surface roughness of the reflection film, and it can prevent the decrease of the reflectance.

The present invention will be described in detail below with reference to more specific exemplary embodiments.

Exemplary Embodiment 1

The structure of the capacitance type electromechanical transducer of Exemplary Embodiment 1 will be described below with reference to FIG. 1A and FIG. 1B. The electromechanical transducer of the present exemplary embodiment has a plurality of elements 1 therein. Although only four elements 1 are provided in FIG. 1A and FIG. 1B, the number of the elements may be any number.

A cell 2 includes a vibration film 7 of single-crystal silicon having a thickness of 1 µm, a space 5, a vibration film supporting portion 4 which supports the vibration film 7 of the single-crystal silicon having a resistivity of 0.01 Ωcm, and a silicon substrate 3. The silicon substrate 3 has a thickness of 300 µm and a resistivity of 0.01 Ωcm. The shape of the vibration film 7 of the present exemplary embodiment is a circle with a diameter of 30 µm, which may also be a quadrangle, a hexagon or the like. The vibration film 7 of the single-crystal silicon is mainly formed of single-crystal silicon, and it does not have a layer with a large residual stress formed thereon, and hence it gives high uniformity among each element 1 to the elements, and it can reduce the dispersion of its transmission and reception performance. An aluminum thin-film 8 with a thickness of approximately 200 nm can be formed in order to enhance the electroconductive characteristics of the vibration film 7 of the single-crystal silicon. In the present structure, the vibration film supporting portion 4 is silicon oxide, which has a height of 300 nm. A gap of a space 5 is 200 nm.

Since the vibration film 7 of the single-crystal silicon and the silicon substrate 3 both have low resistance, they can be used as a first electrode or a second electrode. The capacitance type electromechanical transducer of the present exemplary embodiment can draw an electric signal from the first electrode or the second electrode, by forming a drawing wire on the silicon substrate or preparing a silicon substrate having through-hole interconnections. The drive principle of the reception and the transmission is as described in the part of the above described embodiment.

In the capacitance type electromechanical transducer of the present exemplary embodiment, a stress relaxation layer 9 is arranged on a receiving face, and a light reflection layer 6 is arranged on the stress relaxation layer 9. The stress relaxation layer 9 is made of PDMS, and the light reflection layer 6 is made of gold. The stress relaxation layer 9 has an acoustic impedance of 1.8 MRayls, and a thickness of 100 µm. Since the difference of the acoustic impedance between the stress relaxation layer 9 and the silicon vibration film 7 is extremely small, the acoustic wave is not almost reflected at an interface between the stress relaxation layer and the receiving face. In addition, when the electromechanical transducer of the present embodiment is used in a medium such as water having low acoustic impedance, since the difference of the acoustic impedance between the stress relaxation layer 9 and the medium is extremely small, the reflection of the acoustic wave at an interface between the stress relaxation layer and the medium can be reduced. Consequently, when receiving an acoustic wave, the electromechanical transducer does not cause the deterioration of the strength of the reception signal. The light reflection layer 6 is a layer mainly for reflecting a light with a wavelength which is emitted from a light source to be used for irradiating a subject so as to generate a photoacoustic wave, and it may be a membrane that shows a high reflectance with respect to the wavelength which the light source has. As the light reflection layer 6, aluminum (Al), a dielectric multilayer and the like can also be used. The capacitance type electromechanical transducer of the present exemplary embodiment can be used for receiving a photoacoustic wave, as has been described in the above described embodiment.

Exemplary Embodiment 2

Figure 2:
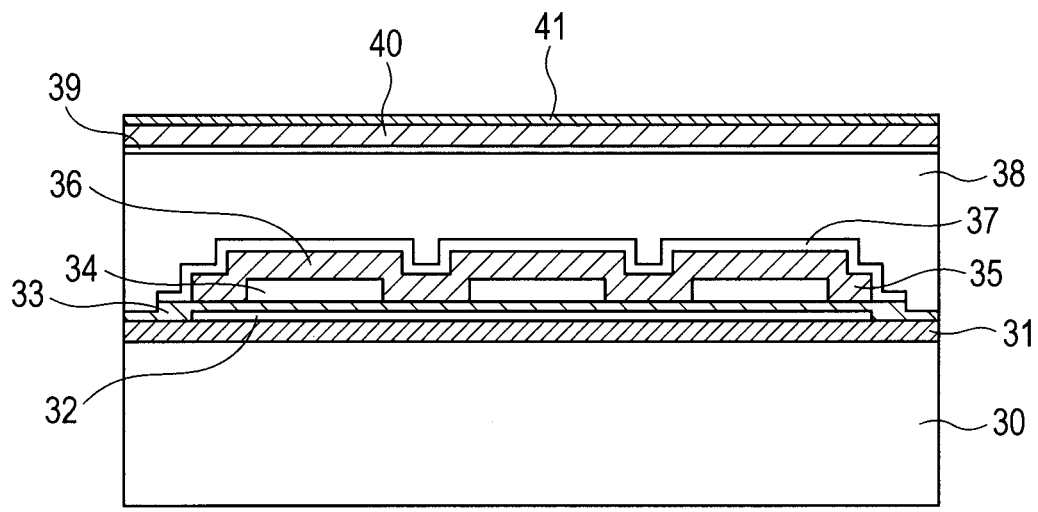
FIG. 2 is a sectional view illustrating an electromechanical transducer in Exemplary Embodiment 2 of the present invention.

The structure of the capacitance type electromechanical transducer of Exemplary Embodiment 2 will be described below with reference to FIG. 2. The electromechanical transducer of Exemplary Embodiment 2 has an approximately similar structure to that of Exemplary Embodiment 1. The cell includes an upper electrode 37, a vibration film 36 with a thickness of 1 µm, a space 34, a vibration film supporting portion 35 which supports the vibration film 36, an insulation membrane 33, a lower electrode 32 and a substrate 30. The substrate 30 is a silicon substrate, the vibration film 36 and the vibration film supporting portion 35 are a silicon nitride film, and the upper electrode 37 and the lower electrode 32 are aluminum. An oxide film 31 is arranged between the substrate 30 and the lower electrode 32, and it insulates both of them from each other. When the substrate 30 is a low-resistance silicon substrate or an insulating substrate made from glass or the like, the oxide film 31 needs not be formed therebetween.

The substrate 30 has a thickness of 300 µm. In the present structure, the shape of the vibration film 36 is a circle with a diameter of 30 µm. The vibration film supporting portion 35 has a height of 300 nm, and it has a gap of the space 34 of 200 nm. A stress relaxation layer 38 is arranged on a receiving face, and a light reflection layer 41 is arranged on the stress relaxation layer 38. The light reflection layer 41 is formed on a high-stiffness supporting layer 40 for the light reflection layer, in order to keep the stiffness of the light reflection layer 41. The high-stiffness supporting layer 40 for the light reflection layer having the light reflection layer 41 is bonded onto the stress relaxation layer 38 by a resin 39.

The stress relaxation layer 38 is made of PDMS. The stress relaxation layer 38 has an acoustic impedance of 1.8 MRayls, and a thickness of 50 µm. The stress relaxation layer 38 desirably has an acoustic impedance of 1 MRayls to 2 MRayls. When the stress relaxation layer has the acoustic impedance of the value, the acoustic wave is not almost reflected at an interface between the stress relaxation layer and the receiving face. Consequently, when receiving an acoustic wave, the electromechanical transducer does not cause the deterioration of the strength of the reception signal. The stress relaxation layer 38 can be produced with a spin coating method, a dropping method, a pressing method using a mold or a method of affixing a stress relaxation layer which has been formed by a mold.

The light reflection layer 41 is made of gold, and the high-stiffness supporting layer 40 for the light reflection layer, which supports the light reflection layer 41, is made of polycarbonate. The supporting layer has a Young's modulus of $2.5 \times 10^9$ Pa, and a thickness of 100 µm. Since the stress relaxation layer 38 has a low Young's modulus, the light reflection layer 41 is occasionally warped or deformed due to the stress or the like of the light reflection layer. In addition, when the adhesiveness between the light reflection layer 41 and the stress relaxation layer 38 is low, the light reflection layer occasionally peels from the stress relaxation layer. In the present structure, since the light reflection layer 41 is formed on the supporting layer 40 for the light reflection layer, which has stiffness higher than that of the stress relaxation layer 38, the light reflection layer can be prevented from being warped or deformed, even when the supporting layer 40 for the light reflection layer is bonded onto the stress relaxation layer 38. In addition, the light reflection layer 41 is supported by the supporting layer 40 for the light reflection layer, and the supporting layer 40 for the light reflection layer and the stress relaxation layer 38 can be bonded to each other with an adhesion method or an adhesive showing high adhesive strength. Consequently, the structure with the use of the supporting layer for the light reflection layer can enhance the adhesive strength, compared to the case in which the light reflection layer is film-formed directly on the stress relaxation layer.

Polycarbonate of the supporting layer 40 for the light reflection layer has an acoustic impedance of 2.4 MRayls. Since the difference of the acoustic impedance among the stress relaxation layer 38, the high-stiffness supporting layer 40 for the light reflection layer and the receiving face is comparatively small, the reflection of the acoustic wave is very small at each interface. Consequently, the electromechanical transducer can receive an acoustic wave signal without lowering the strength. The high-stiffness supporting layer 40 for the light reflection layer may have an approximately equal acoustic impedance to that of the stress relaxation layer 38, and it may also be acrylic, polyimide, polyethylene and the like. The high-stiffness supporting layer 40 for the light reflection layer desirably has an acoustic impedance of 1 MRayls to 5 MRayls. A silicon-based adhesive can be used for a resin 39 for bonding the high-stiffness supporting layer 40 for the light reflection layer to the stress relaxation layer 38. An adhesive of an epoxy resin or the like can also be used. The present exemplary embodiment also shows a similar effect to that of the above described embodiment and the exemplary embodiment.

Exemplary Embodiment 3

The electromechanical transducer in each of the above described exemplary embodiments can be used for a photoacoustic apparatus using a photoacoustic imaging technology. The photoacoustic imaging technology is a technology of: firstly irradiating a subject with a pulse light; making an optical absorber absorb the energy of the light which has propagated/diffused in the subject; thereby receiving the generated acoustic wave; and imaging the information in the inner part of the subject by using the received signal for this acoustic wave. Consequently, the photoacoustic apparatus can obtain the information on the profile of optical properties such as the profile of initial pressure generation and the profile of light absorption coefficient in the subject as an image data.

Figure 3:
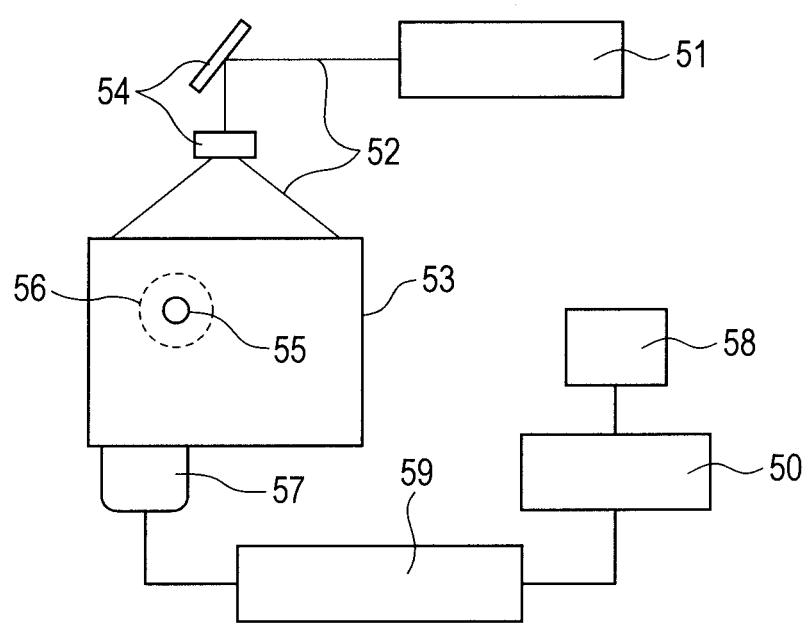
FIG. 3 is a schematic view illustrating a photoacoustic apparatus of the present invention.

FIG. 3 illustrates a schematic view of a photoacoustic apparatus to which the present invention can be applied. The photoacoustic apparatus according to the present invention has at least a light source 51, an electromechanical transducer 57 in each of the above described exemplary embodiments, which is an acoustic wave receiver, a signal-processing section 59 and a data-processing section 50. In the present exemplary embodiment, an oscillating light 52 which has been emitted from the light source 51 irradiates the subject 53 through an optical member 54 such as a lens, a mirror and an optical fiber. In the subject, an optical absorber 55 (for instance, a tumor, a blood vessel and the like) in the subject absorbs the light which has irradiated the subject to generate an acoustic wave 56. The acoustic wave receiver 57 receives the acoustic wave 56, it converts the above described acoustic wave into an electric signal, and then it outputs the electric signal to the signal-processing section 59. The signal-processing section 59 conducts signal processing such as A/D conversion and amplification for an input electric signal, and it outputs the processed signal to the data-processing section 50. The data-processing section 50 converts the input signal into an image data, and it outputs the image data to a display section 58. The display section 58 displays an image based on the input image data.

According to the photoacoustic apparatus of the present invention, an electromechanical transducer which is an acoustic wave receiver can generate an image data containing less noise because the electromechanical transducer has a light reflection film and consequently a light is not incident on the receiving face.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-090123, filed Apr. 14, 2011, which is hereby incorporated by reference herein in its entirety.

What is claimed is:

1. An electromechanical transducer comprising:
at least one cell;
a light reflection layer over the cell; and
a stress relaxation layer provided between the cell and the light reflection layer;
wherein the cell comprises a first electrode and a vibration film having a second electrode formed so as to interpose a space between the first electrode and the second electrode.

2. The electromechanical transducer according to claim 1, wherein the cell further comprises vibration film supporting portion which supports the vibration film so as to form the space between the first electrode and the vibration film.

3. The electromechanical transducer according to claim 1, further comprising a supporting layer for the light reflection layer, which supports the light reflection layer, provided between the stress relaxation layer and the light reflection layer, wherein the supporting layer for the light reflection layer has stiffness higher than that of the stress relaxation layer.

4. The electromechanical transducer according to claim 1, wherein the stress relaxation layer has an acoustic impedance of 1 MRayls or more and 2 MRayls or less.

5. The electromechanical transducer according to claim 1, wherein the stress relaxation layer has a Young's modulus of 100 MPa or less.

6. The electromechanical transducer according to claim 3, wherein the supporting layer for the light reflection layer has an acoustic impedance of 1 MRayls or more and 5 MRayls or less.

7. The electromechanical transducer according to claim 3, wherein the supporting layer for the light reflection layer has a Young's modulus of 100 MPa or more and 20 GPa or less.

8. The electromechanical transducer according to claim 1, wherein the stress relaxation layer is made of polydimethylsiloxane.

9. A photoacoustic apparatus comprising the electromechanical transducer according to claim 1, a light source, and a data-processing apparatus, wherein
the electromechanical transducer receives an acoustic wave generated in a subject irradiated with light from the light source, and converts the acoustic wave into an electric signal, and
the data-processing apparatus generates an image data using the electric signal.

10. The electromechanical transducer according to claim 9, wherein the light reflection layer has a reflectance of 80% or more with respect to the light.

11. An electromechanical transducer comprising:
at least one cell;
a first layer over the cell, the first layer having a reflectance of 80% or more with respect to a light; and
a second layer provided between the cell and the first layer, the second layer having a Young's modulus of 100 MPa or less;
wherein the cell comprises a first electrode and a vibration film having a second electrode formed so as to interpose a space between the first electrode and the second electrode; and
wherein the electromechanical transducer is configured to receive an acoustic wave generated in a subject irradiated with the light.

12. The electromechanical transducer according to claim 11, wherein the cell further comprises a vibration film supporting portion which supports the vibration film so as to interpose the space between the first electrode and the vibration film.

13. The electromechanical transducer according to claim 11, further comprising a third layer which supports the first layer, provided between the first layer and the second layer, wherein the third layer has stiffness higher than that of the second layer.

14. The electromechanical transducer according to claim 11, wherein the second layer has an acoustic impedance of 1 MRayls or more and 2 MRayls or less.

15. The electromechanical transducer according to claim 13, wherein the third layer has an acoustic impedance of 1 MRayls or more and 5 MRayls or less.

16. The electromechanical transducer according to claim 13, wherein the third layer has a Young's modulus of 100 MPa or more and 20 GPa or less.

17. The electromechanical transducer according to claim 11, wherein the second layer is made of polydimethylsiloxane.

18. A photoacoustic apparatus comprising the electromechanical transducer according to claim 11, a light source for the light, and a data-processing apparatus, wherein
- the electromechanical transducer receives an acoustic wave and converts the acoustic wave into an electric signal, and
- the data-processing apparatus generates an image data using the electric signal.

19. The electromechanical transducer according to claim 1, wherein the vibration film comprises a membrane and the second electrode.

20. The electromechanical transducer according to claim 1, wherein the vibration film is the second electrode.

21. The electromechanical transducer according to claim 11, wherein the vibration film comprises a membrane and the second electrode.

22. The electromechanical transducer according to claim 11, wherein the vibration film is the second electrode.

* * * * *